United States Patent
Baynham et al.

(10) Patent No.: US 8,696,616 B2
(45) Date of Patent: Apr. 15, 2014

(54) OBESITY THERAPY AND HEART RATE VARIABILITY

(75) Inventors: Tamara C. Baynham, Piscataway, NJ (US); Jason L. Harris, Mason, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 18 days.

(21) Appl. No.: 12/980,695

(22) Filed: Dec. 29, 2010

(65) Prior Publication Data

US 2012/0172792 A1 Jul. 5, 2012

(51) Int. Cl.
*A61M 37/00* (2006.01)
*A61N 1/00* (2006.01)
*A61M 5/172* (2006.01)
*A61N 1/36* (2006.01)
*A61B 5/024* (2006.01)
*A61B 5/0245* (2006.01)

(52) U.S. Cl.
CPC .............. *A61M 5/1723* (2013.01); *A61N 1/36* (2013.01); *A61N 1/36007* (2013.01); *A61N 1/36085* (2013.01); *A61B 5/02405* (2013.01); *A61B 5/0245* (2013.01)
USPC .......... 604/65; 604/2; 604/40; 604/58; 604/60

(58) Field of Classification Search
CPC ..... A61M 37/00; A61N 1/36; A61N 1/36007; A61N 36/085; A61B 5/024; A61B 5/02405; A61B 5/02438; A61B 5/0245; A61B 5/0402
USPC ........ 604/66, 503; 607/2, 40, 58, 60; 600/509
See application file for complete search history.

(56) References Cited

U.S. PATENT DOCUMENTS

| | | | |
|---|---|---|---|
| 4,515,584 A | 5/1985 | Abe et al. |
| 4,823,808 A | 4/1989 | Clegg et al. |
| 5,188,104 A | 2/1993 | Wernicke et al. |
| 5,231,988 A | 8/1993 | Wernicke et al. |
| 5,263,480 A | 11/1993 | Wernicke et al. |
| 5,398,688 A | 3/1995 | Laniado |
| 5,540,730 A | 7/1996 | Terry, Jr. et al. |
| 5,540,734 A | 7/1996 | Zabara |

(Continued)

FOREIGN PATENT DOCUMENTS

| EP | 377695 A1 | 7/1990 |
|---|---|---|
| WO | WO-8911701 A1 | 11/1989 |

(Continued)

OTHER PUBLICATIONS

Acharya et al., "Heart rate variability: a review," Med Bio Eng Comput (2006) 44:1031-1051.

(Continued)

*Primary Examiner* — Quynh-Nhu H Vu

(57) ABSTRACT

Methods and devices are provided for delivering obesity therapy to a patient. In general, the methods and devices allow for onset of a patient eating solid food, e.g., the patient beginning a meal, to trigger delivery of an obesity therapy to a patient. The obesity therapy can be delivered to the patient for a limited period of time such that the patient stops receiving the obesity therapy prior to a second onset of the patient eating solid food, e.g., the patient beginning a second meal, which can trigger a second delivery of the obesity therapy to the patient for a limited period of time.

21 Claims, 6 Drawing Sheets

(56) References Cited

U.S. PATENT DOCUMENTS

| | | | |
|---|---|---|---|
| 5,707,400 | A | 1/1998 | Terry, Jr. et al. |
| 6,023,009 | A | 2/2000 | Stegemann et al. |
| 6,853,862 | B1 | 2/2005 | Marchal et al. |
| 7,191,007 | B2 | 3/2007 | Desai et al. |
| 7,291,721 | B2 | 11/2007 | Giles-Komar et al. |
| 7,430,450 | B2 | 9/2008 | Imran |
| 7,502,649 | B2 | 3/2009 | Ben-Haim et al. |
| 7,599,743 | B2 | 10/2009 | Hassler, Jr. et al. |
| 7,599,744 | B2 | 10/2009 | Giordano et al. |
| 7,612,182 | B2 | 11/2009 | Giles-Komar et al. |
| 7,664,551 | B2* | 2/2010 | Cigaina ............ 607/40 |
| 7,914,468 | B2 | 3/2011 | Shalon et al. |
| 8,048,169 | B2 | 11/2011 | Burnett et al. |
| 8,182,442 | B2 | 5/2012 | Grau et al. |
| 8,236,023 | B2 | 8/2012 | Birk et al. |
| 8,239,027 | B2 | 8/2012 | Imran |
| 8,346,399 | B2 | 1/2013 | Blomquist |
| 2002/0161414 | A1 | 10/2002 | Flesler et al. |
| 2004/0147816 | A1 | 7/2004 | Policker et al. |
| 2005/0038415 | A1 | 2/2005 | Rohr et al. |
| 2005/0177067 | A1 | 8/2005 | Tracey et al. |
| 2005/0245986 | A1 | 11/2005 | Starkebaum |
| 2005/0277998 | A1 | 12/2005 | Tracey et al. |
| 2005/0288740 | A1 | 12/2005 | Hassler et al. |
| 2006/0020298 | A1 | 1/2006 | Camilleri et al. |
| 2006/0064037 | A1 | 3/2006 | Shalon et al. |
| 2006/0195146 | A1 | 8/2006 | Tracey et al. |
| 2006/0195153 | A1 | 8/2006 | DiUbaldi et al. |
| 2006/0235448 | A1 | 10/2006 | Roslin et al. |
| 2006/0247719 | A1 | 11/2006 | Maschino et al. |
| 2006/0247721 | A1 | 11/2006 | Maschino et al. |
| 2006/0247722 | A1 | 11/2006 | Maschino et al. |
| 2007/0027483 | A1 | 2/2007 | Maschino et al. |
| 2007/0027484 | A1 | 2/2007 | Guzman et al. |
| 2007/0027492 | A1 | 2/2007 | Maschino et al. |
| 2007/0027498 | A1 | 2/2007 | Maschino et al. |
| 2007/0093870 | A1 | 4/2007 | Maschino |
| 2007/0179556 | A1 | 8/2007 | Haim et al. |
| 2007/0185541 | A1 | 8/2007 | DiUbaldi et al. |
| 2007/0203531 | A9 | 8/2007 | Starkebaum |
| 2007/0265598 | A1 | 11/2007 | Karasik |
| 2008/0065168 | A1 | 3/2008 | Bitton et al. |
| 2008/0132962 | A1 | 6/2008 | DiUbaldi et al. |
| 2008/0132968 | A1 | 6/2008 | Starkebaum |
| 2008/0139875 | A1 | 6/2008 | Tracey et al. |
| 2008/0147146 | A1 | 6/2008 | Wahlgren et al. |
| 2009/0062881 | A1 | 3/2009 | Gross et al. |
| 2009/0093858 | A1 | 4/2009 | DiUbaldi |
| 2009/0132018 | A1 | 5/2009 | DiUbaldi et al. |
| 2009/0149918 | A1 | 6/2009 | Krulevitch et al. |
| 2009/0157149 | A1 | 6/2009 | Wahlgren et al. |
| 2009/0192404 | A1 | 7/2009 | Ortiz et al. |
| 2009/0192534 | A1* | 7/2009 | Ortiz et al. ............ 606/157 |
| 2009/0204132 | A1 | 8/2009 | Ortiz et al. |
| 2009/0240194 | A1* | 9/2009 | Keimel et al. ............ 604/66 |
| 2009/0264956 | A1 | 10/2009 | Rise et al. |
| 2010/0032443 | A1 | 2/2010 | Mueller et al. |
| 2010/0049274 | A1 | 2/2010 | Cholette |
| 2010/0056948 | A1* | 3/2010 | Hornby et al. ............ 600/554 |
| 2010/0161001 | A1 | 6/2010 | DiUbaldi et al. |
| 2010/0161005 | A1 | 6/2010 | Wahlgren et al. |
| 2010/0168820 | A1 | 7/2010 | Maniak et al. |
| 2010/0191304 | A1 | 7/2010 | Scott |
| 2010/0211130 | A1 | 8/2010 | Cigaina |
| 2010/0228105 | A1 | 9/2010 | Policker et al. |
| 2010/0234714 | A1* | 9/2010 | Mercier et al. ............ 600/388 |
| 2010/0239648 | A1 | 9/2010 | Smith et al. |
| 2010/0249677 | A1 | 9/2010 | DiUbaldi et al. |
| 2012/0259427 | A1 | 10/2012 | Graham et al. |
| 2013/0116218 | A1 | 5/2013 | Kaplan et al. |

FOREIGN PATENT DOCUMENTS

| | | |
|---|---|---|
| WO | 02/26101 A2 | 4/2002 |
| WO | 2005/041749 A2 | 5/2005 |
| WO | 2006/034400 A2 | 3/2006 |
| WO | 2006/049725 A2 | 5/2006 |
| WO | 2007/007339 A2 | 1/2007 |
| WO | 2007/092390 A2 | 8/2007 |
| WO | 2009/096859 A1 | 8/2009 |
| WO | WO-2009097542 A2 | 8/2009 |
| WO | 2011/032016 A1 | 3/2011 |

OTHER PUBLICATIONS

Ahren et al., "Improved meal-related Beta-cell Function and Insulin Sensitivity by the Dipeptidyl Peptidase-IV Inhibitor Vildagliptin in Metformin-treated Patients With Type 2 Diabetes Over 1 Year," Diabetes Care, 2005, 1936-1940.

Barkeling et al., "Vision and Eating Behavior in Obese Subjects," Obesity Research (2003) 11, 130-134.

Brown et al., "Fructose ingestion acutely elevates blood pressure in healthy young humans," Am J Physiol Regal Integr Comp Physiol 924: R730-R737, 2008.

Buhwald et al., "Baraiatric Surgery: A Systematic Review and Meta-analysis," JAMA, 2004, 1724-1737.

Camilleri et al., "Intra-abdominal vagal blocking (VBLOC therapy): Clinical results with a new implantable medical device," Surgery (2008) vol. 143(6), 723-31.

Codman® 3000 Implantable Constant-Flow Infusion Pump brochure 2003.

Codman® 3000 Implantable Constant-Flow Infusion Pump brochure 2008.

Drucker et al. "The Incretin System: Glucagon-like Peptide-1 Receptor Agonists and Dipeptidyl Peptidase-4 Inhibitors in Type 2 Diabetes," Lancet, 2006, 1696-1705.

Effects of Thickened Feeding on Gastroesophageal Reflux in Infants: A Placebo-Controlled Crossover Study Using Intraluminal Impedance, Pediatrics 111(4), e355-e359 (Apr. 2003).

Friesen et al., "Autonomic Nervous System Response to a Solid Meal and Water Loading in Healthy Children: Its Relation to Gastric Myoelectrical Activity," Neurogastroenterol Motil. 19(5): 376-382 (2007).

Friesen et al., "The Effect Of A Meal And Water Loading On Heart Rate Variability in Children With Functional Dyspepia," Dig Dis Sci 55: 2283-2387 (2010).

Frokjaer et al. "Gut Sensations in Diabetic Autonomic Neuropathy," Pain, 2007, 320-329.

Gameiro et al. "The Neurotransmitters Glycine and GABA Stimulate Glucagon-like Peptide-1 Release From the GLUTag Cell Line," J Physiol, 2005, 761-772.

Geliebter et al., "Gastric Distension by Balloon and Test-Meal Intake in Obese and Lean Subjects," Am J Clin Nutr, vol. 48, 592-594 (1988).

Hansen et al., "Neural Regulation of Glucagon-like Peptide-1 Secretion in Pigs," Am J Physiol Endocrinol Metab, 2004, E939-947.

Iyriboz et al., "Accuracy of pulse oximeters in estimating heart rate at rest and during exercise," Br J Med 1991, 25(3).

Laferrere et al., "Incretin Levels and Effect Are Markedly Enhanced 1 Month After Roux-En-Y Gastric Bypass Surgery in Obese Patients With Type 2 Diabetes," Diabetes Care 30: 1709-1716, 2007.

Lipsitz et al., "Hemodynamic and Autonomic Nervous System Responses to Mixed Meal Ingestion in Healthy Young and Old Subjects and Dysautonomic Patients With Postprandial Hypotension," Circulation, 87: 391-400 (1993).

Lu et al, "Postprandial Changes of Sympathovagal Balance Measured by Heart Rate Variability," Digestive Diseases and Sciences (1999) vol. 44 (4) 857-861.

Lui et al., "Therapeutic Potential of Duodenal Electrical Stimulation for Obesity: Acute Effects on Gastric Emptying and Water Intake," Am J Gastroenterol, 2005, 792-796.

Nauck et al., "Release of Glucagon-like Peptide 1 (GLP-1 [7-36 amide]), Gastric Inhibitory Polypeptide (GIP) and Insulin in

(56) References Cited

OTHER PUBLICATIONS

Response to Oral Glucose After Uppe and Lower Intestinal Restrictions," Zeitschrift fur Gastroenterologie 34: 159-166, 1996.
Nederkoorn et al., "Cephalic phase responses, craving and food intake in normal subjects," Appetite. Aug. 2000; 35(1):45-55(11).
Nederkoorn et al., "Cue reactivity and regulation of food intake," Eat Behav. 2002 Spring; 3(1):61-72.
Nederkoorn et al., "Exposure to binge food in bulimia nervosa: finger pulse amplitude as a potential measure of urge to eat and predictor of food intake," Appetite. Apr. 2004; 42(2):125-130.
Niskanen et al., "Software for advanced HRV analysis," Computer Methods and Programs in Biomedicine (2004) 76, 73-81.
Paintal, et al., "A Study Of Gastric Stretch Receptors: Their Role In The Peripheral Mechanisms Of Satiation Of Hunger And Thirst," Journal of Physiology, vol. 126, 255-270 (1954).
Pumprla et al., "Functional assessment of heart rate variability: physiological basis and practical applications," Intenational Journal of Cardiology 84 (2002) 1-14.
Regional Postprandial Differences in pH Within the Stomach and Gastroesophageal Junction, Digestive Diseases and Sciences, vol. 50, No. 12 (Dec. 2005), pp. 2276-2285.
Reiman et al., "Characterization and Functional Role of Coltage Gated Cation Conductances in the Glucagon-Like Peptide-1 Secreting GLUTag cell line," J Physiol, 2005, 161-175.
Rocca et al, "Role of the Vagus Nerve in Mediating Proximal Mutrient Glucagon-like Peptide-1 Secretion," Endocrinology, 1999, 1687-1694.
Rubino et al., "The Early Effect of the Roux-en-Y Gastric Bypass on Hormones Involved in Body Weight Regulation and Glucose Metabolism," Ann Surg, 2004, 236-242.
Sanmiguel et al., "The TANTALUS TM System for Obesity: Effect on Gastric Emptying of Solids and Ghrelin Plasma Levels," Obesity Surgery vol. 17(11), 1503-09.
Schnabel et al. "Metabolic Effects of the Incretin Exenatide in the Treatment of Type 2 Diabetes," VAS, Health Risk Manag., 2006, 69-77.
Silny et al, "Verification of the intraluminal multiple electrical impedance measurement for the recording of gastrointestinal motility," Nueroogastroenterology & Motility, vol. 5(2): 107-122 (Jun. 1993).
Small et al, "Gut Hormones and the Control of Appetite," Trends Endocrinol Metab, 2004, 259-263.
Spiller et al., "The Ideal Break-inhibition of Jejunal Motility After Ideal Fat Perfusion in Man," Gut, 1984, 365-374.
Task Force of the European Society of Cardiology and the North American Society of Pacing and Electrophysiology, "Heart rate variability," European Heart Journal (1996) 17, 354-381.
Theodorakis et al., "Human Duodenal Entereoendocrine Cells, Source of Both Incretin Peptides, FLP-1 and CIP," Am J Pysio Endocrinol Metab, 2006, E550-559.
Toft-Nielsen et al., "Continuous Subcutaneous Infusion of Glucagon-like Peptide-1 Lowers Plasma Glusoe and Reduces Appetite in Type 2 Diabetic Patents," Diabetes Care, 1999, 1137-1143.
Toft-Nielsen et al., "Determinants of the Impaired Secretion of Glucogon-Like Peptide-a in Type 2 Diabetic Patents," J Clin Endocrinol Metab, 2001, 3717-3723.
U.S. Appl. No. 12/605,409, filed Oct. 26, 2009.
U.S. Appl. No. 12/980,659, filed Dec. 29, 2010.
U.S. Appl. No. 12/980,710, filed Dec. 29, 2010.
Vahl et al., "Effects of GLP-1(7-36)NH2, GLP-1(7-37), and GLP-1-(9-36)NH2 on Intravenous Glucose Tolerance and Glucose-induced Insulin Secretion in Healthy Humans," J Clin Endocrinol Metal, 2003 1772-1779.
Vahl et al., "Glucagon-Like Peptide-1 (GLP-1) Receptors Expressed on Nerve Terminals in the Portal Vein Mediate the Effects of Endogenous GLP-1 on Glucose Tolerance in Rats," Endocrinology, 2007, 4965-4973.
Watanabe et al., "Effects of water ingestion on gastric electrical activity and heart rate variability in healthy subjects," J Auton Neuro Syst 58(1 2): 44-50 (1996).

Whitson et al., "Entero-Endocrine Changes After Gastric Bypass in Diabetic and Nondiabetic Patients: A Preliminary Study," J Surg Res 141: 31-39, 2007.
Wu et al., "A Pilot Study to Evaluate the Effect of Splanchic Nerve Stimulation on Body Composition and Food Intake in Rats," Obesity Surgery (2009) vol. 19(11), 1581-85.
Yacin et al., "Pulse rate variability and gastric electric power in fasting and postprandial conditions," 31st Annual International Conference of the IEEE EMBS Minneapolis, MN, Sep. 2-6, 1999.
Yao et al., "Retrograde Gastric Pacing Reduces Food Intake and Delays Gastric Emptying in Humans: A Potential Therapy for Obesity?" Digestive Diseases and Sciences (2005) vol. 50(9), 1569-75.
Yin et al., "Inhibitory Effects of Intestinal Electrical Stimulation on Food Intake, Weight Loss, and Gastric Emptying in Rats," Am J Physiol Regul Integr Comp Physiol, 2007, R78-82.
Yin et al., "Inhibitory Effects of Stress on Postprandial Gastric Myoelectrical Activity and Vagal Tone in Healthy Subjects," Neurogastroenterol Motil 16(6): 737-744 (Dec. 2004).
Yin et al., "Potential of Intestinal Electrical Stimulation for Obesity: A Preliminary Canine Stidy," Obesity, 2007, 1133-1138.
Zhang et al., "Prokineticin 2 is a target Gene of Roneural Basic Helix-loop-helix Factors for Olfactory Bulb Neurogenesis," J Biol Chem, 2007, 6917-6921.
International Search Report and Written Opinion for PCT/US2011/065031 dated Feb. 9, 2012.
International Search Report and Written Opinion for PCT/US2011/065034 dated Apr. 12, 2012.
Abell et al., Electrogastrography. Current assessment and future perspectives. Dig Dis Sci. Aug. 1988;33(8):982-92.
Amft et al., Analysis of chewing sounds for dietary monitoring. UbiComp 2005: Proceedings of the 7th International Conference on Ubiquitous Computing. Sep. 2005. Tokyo, Japan. pp. 56-72.
Amft, Automatic dietary monitoring using on-body sensors: Detection fo eating and drinking behaviour in healthy individuals. Dissertation submitted to Chemnitz University of Technology. Germany. 2008, 242 pages.
Amft et al., Methods for detection and classification of normal swallowing from muscle activation and sound. 2006, 10 pages.
Amft et al., On-body sensing solutions for automatic dietary monitoring. Wearable Computing and Healthcare. Persuasive computing 2009. pp. 62-70.
Gualdi-Russo et al., Influence of various factors on the measurement of multifrequency bioimpedance. HOMO 2002;53(1):1-16.
Heart rate variability: standards of measurement, physiological interpretation and clinical use. Task Forice of the European Society of Cardiology and the North American Society of Pacing and Electrophysiology. European Heart Journal. 1996;17:354-381.
Hsiao et al., Accuracy and precision of two in-shoe pressure; measurement systems. Ergonimics. Jun. 20, 2002;45(8):537-55.
Junker et al., Gesture spotting with body-worn inertial sensors to detect user activites. Nov. 14, 2007. 30 pages.
Kanaley et al., Plasticity of heart rate signalling and complexity with; exercise training in obese individuals with and without type 2 diabetes. Int J; Obes (Lond). Oct. 2009;33(10):1198-206. doi: 10.1038/ijo.2009.145 Epub Aug. 4, 2009.
Lin et al., Postprandial response of gastric slow waves: Correlation of serosal recordings with electrogastrogram. Digestive Diseases and Sciences. Apr. 2000;45(4):645-651.
Makeyev, Auromatic method of acoustical swalloing detection for monitoring of ingestive behavior. Dissertation. Coulter Scool of Engineering. Apr. 13, 2010. 126 pages.
Melissas et al., Alterations of Global Gastrointestinal Motility After Sleeve; Gastrectomy: A Prospective Study. Ann Surg. Nov. 15, 2012. Abstract.
Millis et al., Association of body fat percentage and heart rate variability; measures of sympathovagal balance. Life Sci. Jan. 30, 2010;86(5-6):153-7. doi: 10.1016/j.ifs.2009.11.018. Epub Dec. 1, 2009.
Nolan et al., Sex-based differences in the association between duration of type 2 diabetes and heart rate variability. Diab Vasc Dis Res. Oct. 2009;6(4):276-82.

(56) References Cited

OTHER PUBLICATIONS

Parker et al., Postprandial mesenteric blood flow in humans: relationship to endogenous gastrointestinal hormone secretion and energy content of food. Eur J Gastroenterol Hepatol. May 1995;7(5):435-40. Abstract.

Sazonov et al., Reply to comment on non-invasive monitoring of chewing and swallowing for objective quantification of ingestive behavior. Physiological Measurement. 2009;30:L5-L7.

Sazonov et al., Toward objective monitoring of ingestive behavior in free-living population. Obesity (Silver Spring). Oct. 2009;17(10):1971-5.

Wesrerterp-Plantenga et al., Deceleration in cumulative food intake curves, changes in body temperature and diet-induced thermogenesis. Physiol Bev. Dec. 1990;48(6):831-6.

Yamaguchi et al., Evaluation of gastrointestinal motility by computerized analysis of abdominal auscultation findings. J Gastroenterol Hepatol. Mar. 2006;21(3):510-4.

Habas et al., Metabolic and Cardiovascular Responses to Liquid and Solid Test Meals, British Journal of Nutrition (1998), 79, 241-247.

\* cited by examiner

OBESITY THERAPY AND HEART RATE VARIABILITY

CROSS REFERENCE TO RELATED APPLICATIONS

The present application is being filed concurrently with U.S. application Ser. No. 12/980,710 entitled "Obesity Therapy And Heart Rate Variability," which is hereby incorporated by reference herein in its entirety.

FIELD OF THE INVENTION

The present invention relates to obesity therapy and heart rate variability.

BACKGROUND OF THE INVENTION

Obesity is becoming a growing concern, particularly in the United States, as the number of people with obesity continues to increase and more is learned about the negative health effects of obesity. Severe obesity, in which a person is 100 pounds or more over ideal body weight, in particular poses significant risks for severe health problems. Accordingly, a great deal of attention is being focused on treating obese patients.

Surgical procedures to treat severe obesity have included various forms of gastric and intestinal bypasses (stomach stapling), biliopancreatic diversion, adjustable gastric banding, vertical banded gastroplasty, gastric plications, and sleeve gastrectomies (removal of all or a portion of the stomach). Such surgical procedures have increasingly been performed laparoscopically. Reduced postoperative recovery time, markedly decreased postoperative pain and wound infection, and improved cosmetic outcome are well established benefits of laparoscopic surgery, derived mainly from the ability of laparoscopic surgeons to perform an operation utilizing smaller incisions of the body cavity wall. However, such surgical procedures risk a variety of complications during surgery, pose undesirable postoperative consequences such as pain and cosmetic scarring, and often require lengthy periods of patient recovery. Patients with obesity thus rarely seek or accept surgical intervention, with only about 1% of patients with obesity being surgically treated for this disorder. Furthermore, even if successfully performed and initial weight loss occurs, surgical intervention to treat obesity may not result in lasting weight loss, thereby indicating a patient's need for additional, different obesity treatment.

Surgical procedures to treat severe obesity can affect a patient's hormone levels. It has been noted, for example in Ann Surg (2004) 240: 236-242, that a Roux-en-Y gastric bypass surgery performed on a patient can affect the patient's hormones involved in body weight regulation and glucose metabolism. A number of studies in patients after bariatric surgery suggest that the incretin pathway contributes to improvements in Type 2 Diabetes and to weight loss. Specifically, there are increases in meal-related circulating Glucagon-Like Peptide (GLP-1) levels after surgery, as noted for example in Laferrere et al., "Incretin Levels And Effect Are Markedly Enhanced 1 Month After Roux-En-Y Gastric Bypass Surgery In Obese Patients With Type 2 Diabetes," Diabetes Care 30: 1709-1716, 2007, and Whitson et al., "Entero-Endocrine Changes After Gastric Bypass In Diabetic And Nondiabetic Patients: A Preliminary Study," J Surg Res 141: 31-39, 2007. However, so affecting hormonal level effects with surgery incurs the adverse consequences of surgery, e.g., risk of complications, undesirable postoperative consequences, lengthy recovery time, etc.

Accordingly, there remains a need for methods and devices for treating obesity and for methods and devices for affecting a patient's hormone levels.

SUMMARY OF THE INVENTION

The present invention generally provides methods and devices for obesity therapy. In one embodiment, a medical system is provided that includes a sensor, a processor, and a delivery device. The sensor is configured to be positioned in contact with a tissue of a patient, and configured to sense a heart rate of the patient. The processor is configured to be in communication with the sensor and to analyze the sensed heart rate to detect a change in heart rate of the patient. The delivery device is configured to be implanted within the patient and to be in communication with the processor. The delivery device is defaulted to a dormant mode in which the delivery device does not deliver an obesity therapy to the patient, and the delivery device is configured to change from the dormant mode to a delivery mode, in which the delivery device delivers the obesity therapy to the patient, in response to the processor detecting the change in heart rate.

The sensor can be configured to be implanted within the patient, or the sensor can be configured to be transcutaneously positioned such that the sensor is in direct contact with an exterior skin surface of the patient. If the sensor is configured to be implanted within the patient, the sensor can include at least one of a lead configured to be implanted within a heart of the patient, and an electrode configured to be implanted on a thorax of the patient. If the sensor is configured to be transcutaneously positioned, the sensor can include at least one of a first electrode attached to a strap configured to be worn by the patient such that the first electrode is positioned on an exterior skin surface of a chest of the patient, a second electrode attached to an article of clothing configured to be worn by the patient such that the second electrode contacts an exterior skin surface of the patient, a pulse oximeter configured to be positioned on an external skin surface of a finger of the patient, and a third electrode attached to a band configured to be positioned around a wrist of the patient such that the third electrode contacts an exterior skin surface of a wrist of the patient.

The processor can be configured to be implanted within the patient, or the processor can be configured to be transcutaneously positioned. The processor can be configured to detect the change in heart rate in any number of ways. In one embodiment, the processor can be configured to detect the change in heart rate by analyzing electrocardiogram (ECG) signals sensed by the sensor. The analyzing can include analyzing a power spectral density in low frequency and high frequency bands to determine onset of the patient eating a solid food.

The delivery device can have a variety of configurations. In one embodiment, the delivery device can be configured to change from the delivery mode to the dormant mode upon occurrence of a predetermined trigger event, and can be configured to repeatedly change between the delivery and dormant modes based on the processor detecting changes in heart rate of the patient and based on occurrences of the predetermined trigger event. The predetermined event can include, e.g., passage of a predetermined amount of time during which the delivery device is in the delivery mode.

The obesity therapy can include any one or more therapies. In one embodiment, the obesity therapy can include at least one of electrical stimulation and administration of a therapeutic agent to the patient. The therapeutic agent can include a nutrient configured to provoke a release of one or more hormones from L-cells of the patient.

In another embodiment, a medical system is provided that includes a sensor, a processor, and a delivery device. The sensor is configured to be positioned in contact with a tissue of a patient to gather data. The gathered data includes at least one of pH levels in a stomach of the patient and a heart rate of the patient. The processor is configured to be in communication with the sensor and to analyze the sensed data to determine onset of solid food ingestion by the patient. The delivery device is configured to be implanted within the patient and to be in communication with the processor. The delivery device is defaulted to a dormant mode in which the delivery device does not deliver an obesity therapy to the patient, and the delivery device is configured to change from the dormant mode to a delivery mode, in which the delivery device delivers the obesity therapy to the patient, in response to the processor determining onset of the solid food ingestion. The obesity therapy includes electrical stimulation of the patient and administration of a chemical to the patient.

The sensor can be configured to be implanted within the patient, or the sensor can be configured to be transcutaneously positioned such that the sensor is in direct contact with an exterior skin surface of the patient. In one embodiment, the sensor can be configured to gather data including the pH levels in a stomach of the patient and the heart rate of the patient. The processor can be configured to analyze the pH levels and the heart rate to determine onset of the solid food ingestion. In another embodiment, the sensor can be configured to gather data including only one the pH levels in a stomach of the patient and the heart rate of the patient, and the processor can be configured to analyze only the one of the pH levels and the heart rate to determine onset of the solid food ingestion.

The processor can be configured to be implanted within the patient, or the processor can be configured to be transcutaneously positioned. The processor can be configured to detect the change in heart rate in any number of ways. In one embodiment, the processor can be configured to analyze the sensed heart rate data by analyzing a power spectral density in low frequency and high frequency bands to determine onset of the solid food ingestion.

The delivery device can have a variety of configurations. In one embodiment, the delivery device can be configured to be implanted in an intestine of the patient, to electrically stimulate the intestine when the delivery device is in the delivery mode, and to administer the chemical in the intestine when the delivery device is in the delivery mode. In another embodiment, the delivery device can be configured to change from the delivery mode to the dormant mode upon occurrence of a predetermined trigger event, and can be configured to repeatedly change between the delivery and dormant modes based on the processor determining onsets of solid food ingestion and based on occurrences of the predetermined trigger event. The predetermined trigger event can include, e.g., passage of a predetermined amount of time during which the delivery device is in the delivery mode. The delivery device can include a reservoir. The reservoir can be configured to contain a supply of the chemical and to release a partial portion of the chemical supply each time the delivery device is in the delivery mode.

The obesity therapy can include any one or more therapies. In one embodiment, the chemical can include a nutrient configured to provoke a release of one or more hormones from L-cells of the patient.

In another aspect, a medical method is provided that includes positioning a sensing device in contact with tissue of a patient, positioning a delivery device including an obesity therapy and being in a default off configuration in contact with tissue of the patient, detecting a change in heart rate of a patient using heart rate data gathered by the sensing device, and, in response to the detected change in heart rate, changing the delivery device from the default off configuration, in which the delivery device does not deliver the obesity therapy to the patient, to an on configuration in which the delivery device delivers the obesity therapy to the patient.

The change in heart rate can be detected in any number of ways. For example, the change in heart rate can be detected using a processor remotely located from the delivery device, and the change in heart rate can be transmitted from the processor to the delivery device to trigger the changing. For another example, detecting the change in heart rate can include analyzing a power spectral density in low frequency and high frequency bands of the heart rate data to determine onset of the patient eating a solid food.

Positioning the sensing device can include transdermally positioning the sensing device such that the sensing device is in direct contact with an exterior skin surface of the patient, or positioning the sensing device can include implanting the sensing device within the patient.

The obesity therapy can include any one or more therapies. In one embodiment, the obesity therapy can include at least one of electrically stimulating the patient and administering a therapeutic agent to the patient. In another embodiment, the method can include orally administering a nutrient to the patient in conjunction with the patient eating solid food, and the obesity therapy can include electrically stimulating the patient.

In another embodiment, a medical method is provided that includes determining an onset of solid food ingestion by a patient by detecting a change in heart rate of the patient, and, in response to the detection of the change in heart rate, starting delivery of an obesity therapy to the patient. The obesity therapy includes at least one of electrical stimulation of a tissue of the patient and administration of a nutrient to the patient. The nutrient is configured to provoke a release of one or more hormones from L-cells of the patient. In some embodiments, after starting delivery of the obesity therapy, delivery of the obesity therapy can be stopped when a predetermined trigger event occurs, and the starting and the stopping can be repeated such that the obesity therapy is intermittently delivered to the patient.

In another embodiment, a medical method is provided that includes determining an onset of solid food ingestion by a patient by detecting a change in heart rate of the patient and a change in a pH level in a stomach of the patient, and, in response to the detection of the change in heart rate and the change in the pH level, starting delivery of an obesity therapy to the patient. The obesity therapy includes electrical stimulation of a tissue of the patient and administration of a chemical to the patient. The chemical can include, e.g., a nutrient.

The method can vary in any number of ways. For example, after starting delivery of the obesity therapy, delivery of the obesity therapy can be stopped when a predetermined trigger event occurs, and the starting and the stopping can be repeated such that the obesity therapy is intermittently delivered to the patient. For another example, the electrical stimulation can be delivered to the patient at a first location, and the chemical can be administered to a patient at a second, substantially different location. In one embodiment, the first location can include an intestine of the patient, and the second location can include a stomach of the patient.

In another aspect, a computer readable medium is provided having a program stored thereon. The program causes a computer to perform the steps of determining an onset of solid food ingestion by a patient by detecting a change in heart rate of the patient and a change in a pH level in a stomach of the patient, and, in response to the detection of the change in heart rate and the change in the pH level, starting delivery of an obesity therapy to the patient. The obesity therapy includes electrical stimulation of a tissue of the patient and administration of a chemical to the patient.

BRIEF DESCRIPTION OF THE DRAWINGS

The invention will be more fully understood from the following detailed description taken in conjunction with the accompanying drawings, in which.

DETAILED DESCRIPTION OF THE INVENTION

Figure 1:
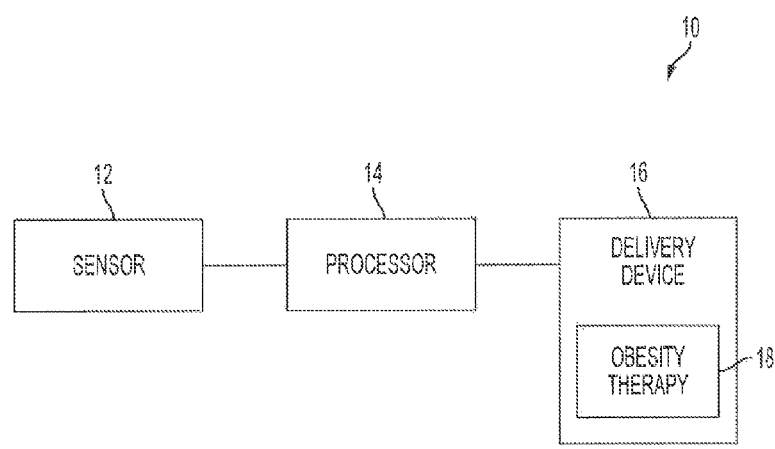
FIG. 1 is a schematic view of one embodiment of an obesity therapy system including a sensor, a processor, and a delivery device for delivering an obesity therapy to a patient.

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

Various exemplary methods and devices are provided for delivering obesity therapy to a patient. In general, the methods and devices allow for onset of a patient eating solid food, e.g., the patient beginning a meal, to trigger delivery of an obesity therapy to a patient. The obesity therapy can be delivered to the patient for a limited period of time such that the patient stops receiving the obesity therapy prior to a second onset of the patient eating solid food, e.g., the patient beginning a second meal, which can trigger a second delivery of the obesity therapy to the patient for a limited period of time. In other words, a patient can intermittently receive obesity therapy throughout a period of hours, days, weeks, months, etc., with each delivery of the obesity therapy coinciding with intake of solid food. By providing obesity therapy in conjunction with eating, the obesity therapy can be most effective in treating obesity and/or encouraging weight loss.

Generally, methods and devices are provided that allow for a determination of when a patient begins eating solid food based on analysis of the patient's heart rate and/or pH levels in the patient's digestive tract. In an exemplary embodiment, an obesity therapy system can include a sensor, such as a heart rate sensor, and a delivery device in communication with the heart rate sensor. The heart rate sensor can be configured to gather heart rate data for a patient. The delivery device can be configured to trigger delivery of an obesity therapy to the patient based on changes in the sensed heart rate data. A patient's heart rate can change when the patient begins eating solid food, thereby allowing changes in heart rate, e.g., heart rate variability (HRV) to reliably indicate onset of a meal.

Alternatively or in addition to an obesity therapy system including a delivery device and a heart rate sensor, the obesity therapy system can include a pH sensor configured to gather digestive tract pH levels of the patient, e.g., pH levels within a patient's stomach. The delivery device can be configured to begin delivery of the obesity therapy to the patient based on changes in the sensed pH levels data. If the system also includes the heart rate sensor, the delivery device can be configured to begin delivery of the obesity therapy to the patient based on the sensed pH levels data alone, based on the sensed heart rate data alone, or based on both the sensed pH levels data and the sensed heart rate data. The obesity therapy delivered to the patient can include one or more obesity therapies. Non-limiting examples of obesity therapies include electrical stimulation of tissue, e.g., a stomach wall of the patient, an intestinal wall of the patient, individual nerves or nerve bundles innervating a target tissue of interest, etc., and administration of a therapeutic agent, e.g., a nutrient, a hormone, etc. A heart rate sensor and/or a pH level sensor can each be defaulted to a default dormant mode and can be configured to change to a delivery configuration upon the occurrence of a triggering event, e.g., upon a detected change in heart rate and/or pH levels. In this way, the sensor(s) can conserve power and controllably, sporadically deliver obesity therapy to a patient.

In an exemplary embodiment, illustrated in FIG. 1, an obesity therapy system 10 can include a sensor 12 configured to gather data from a patient, a processor 14 configured to analyze data, and a delivery device 16 configured to deliver an obesity therapy 18 to the patient. As discussed in further detail below, the sensor 12, the processor 14, and the delivery device 16 can each have a variety of sizes, shapes, and configurations. Generally, the sensor 12 can be configured to gather data from a patient regarding at least one of a heart rate of the patient and a gastric pH of the patient. A heart rate sensor can be subcutaneously positioned, e.g., implanted within a patient, e.g., at the distal esophagus, the proximal stomach, and the mid/distal stomach, etc., or can be transcutaneously positioned, e.g., positioned external to a patient such as positioned on an external skin surface thereof. A gastric pH sensor can be subcutaneously positioned, such as within a gastrointestinal tract of a patient, e.g., within the patient's stomach, within the patient's intestine, etc. The sensor 12 can be configured to be in communication with the processor 14 such that the sensor 12 can communicate sensed data to the processor 14 through wired and/or wireless transmission.

Generally, the processor 14 can be configured to receive data gathered by the sensor 12 and to analyze the gathered data to determine whether the patient started eating solid food. Non-limiting examples of the processor 14 include a microprocessor and a computer readable medium having a program stored thereon, the program being configured to cause a computer to perform one or more steps. The sensor 12 can be configured to transmit gathered data to the processor 14 in real time such that the processor 14 can analyze relatively recent data and relatively quickly begin analysis thereof, as will be appreciated by a person skilled in the art. In this way, the processor 14 can make a relatively quick determination as to whether the patient has begun eating solid food. Based on the analysis, the processor 14 can be configured to trigger the delivery device 16 to begin delivery of the obesity therapy 18 to the patient. In other words, if the processor 14 determines from the gathered data that the patient started eating solid food, the processor 14 can communicate a trigger signal to the delivery device 16 to trigger the delivery device's delivery of the obesity therapy 18 to the patient. The processor 14 and the delivery device 16 can be in wired and/or wireless communication with one another. Because the processor 14 can relatively quickly receive and analyze data gathered by the sensor 12, as mentioned above, and can relatively quickly, e.g., instantaneously or near instantaneously, communicate such a determination to the delivery device 16, the delivery device 16 can consequently start delivery of the obesity therapy 18 to the patient relatively soon after the onset of the patient eating solid food.

The trigger signal can have a variety of configurations, such as a simple on/off signal configured to change the delivery device 16 from a dormant or off mode, in which the delivery device 16 does not deliver the obesity therapy 18 to the patient, to a delivery or on mode in which the delivery device 16 delivers the obesity therapy 18 to the patient. The trigger signal can trigger a timer at the delivery device 16 that can initiate delivery of the obesity therapy 18 after a predetermined period of time has passed, e.g., 15 minutes, etc., such that the obesity therapy 18 can be initiated a certain amount of time after the detection of a meal has occurred. The trigger signal can optionally include data related to the solid food ingested by the patient, e.g., an amount or estimated amount of food eaten. The delivery device 16 can be configured to communicate such solid food data to an external storage unit for subsequent analysis. Alternatively or in addition, the delivery device 16 can be configured to use such solid food data to determine an amount of the obesity therapy 18 to deliver to the patient, e.g., a certain volume of chemical to be delivered thereto, and/or a length of time to deliver the obesity therapy to the patient. Alternatively, the processor 14 can be configured to include with the trigger signal instructions regarding the amount of the obesity therapy 18 to deliver to the patient and/or the length of time to deliver the obesity therapy to the patient. In some embodiments, after transmitting the trigger signal to the delivery device 16, the processor 14 can be configured to transmit a second, subsequent trigger signal to the delivery device 16 to cause the delivery device 16 to stop delivering the obesity therapy 18 to the patient. The second, subsequent trigger signal can be sent for any number of reasons, such as after a certain period of time or if, based on sensed data gathered the sensor 12, the processor 14 determines that the patent has ceased eating solid food.

Upon receipt of the trigger signal, the delivery device 16 can be configured to deliver the obesity therapy 18 to the patient for any length of time. In one embodiment, the trigger signal can be configured to trigger delivery of the obesity therapy 18 for an indefinite period of time. In other words, the delivery device 16 can be configured to have a default off mode in which the delivery device 16 does not deliver the obesity therapy 18 to the patient, and be configured to permanently switch to an on mode during which the delivery device 16 delivers the obesity therapy 18 to the patient. The indefinite period of time can be defined by an amount of the obesity therapy 18 available to the delivery device 16, e.g., if the delivery device 16 includes a finite supply of the a chemical obesity therapy 18, can be defined by an amount of power available to the delivery device 16, e.g., battery life, and/or can be defined by a likely-unknown period of time before a predetermined termination event occurs that triggers an end of the obesity therapy's delivery to the patient. The predetermined termination event can include, e.g., an end of the patient eating solid food as determined by the processor 14 and communicated from the processor 14 to the delivery device 16. In another embodiment, the trigger signal can be configured to trigger delivery of the obesity therapy 18 for a predetermined time period, e.g., a period of "N" seconds, minutes, etc. in which the delivery device 16 is configured to deliver the obesity therapy 18 to the patient before stopping delivery thereof if and until the processor 14 communicates another trigger signal to the delivery device 16 to again start delivery of the obesity therapy 18. The delivery device 16 can therefore be configured to intermittently deliver the obesity therapy 18 to the patient. In other words, the delivery device 16 can be configured to have a default off mode in which the delivery device 16 does not deliver the obesity therapy 18 to the patient, and be configured to change from the off mode to an on mode for the predetermined time period during which the delivery device 16 delivers the obesity therapy 18 to the patient before returning to the off mode. Further, triggering delivery of the obesity therapy 18 at generally unpredictable intervals, e.g., whenever the patient eats solid foods, can help prevent the body from adapting to a particular obesity therapy by learning to expect the therapy at certain times.

The delivery device 16 can be configured to deliver to the patient any one or more obesity therapies 18 configured to provide therapeutic treatment of obesity to the patient. In one exemplary embodiment, the obesity therapy 18 can include electrical stimulation of the patient, e.g., tissue or nerves thereof. Because the delivery device 16 can be configured to intermittently deliver the obesity therapy 18 to the patient once triggered to begin delivery thereof to the patient, nerve and/or tissue desensitization to electrical signals and nerve and/or tissue damage can be reduced, if not entirely prevented, because the electrical signal is not being continuously delivered to the nerve and/or tissue. Moreover, when triggered to begin delivery of the obesity therapy 18 by the processor 14, the delivery device 16 can be configured to noncontinuously deliver the electrical signal to the patient such that the signal is alternately "off" and "on" when the delivery device 16 is in the on mode. The periods of time in which the signal is "off" and "on" can be the same or different from one another. In an exemplary embodiment, the signal can be "off" for a longer period of time than it is "on," which can help reduce, if not prevent, nerve and/or tissue desensitization to electrical signals and nerve and/or tissue damage. Delivering an electrical signal that is "off" for a longer period of time than it is "on" can also help conserve power, e.g., reduce battery consumption, and can reduce a size of a power supply required to power the delivery device 16. However, the delivery device 16 can be configured to continuously deliver the electrical signal to the patient, e.g., continuously delivered indefinitely or continuously delivered during the predetermined time period of "N" minutes after the processor 14 triggers the delivery device 16.

The electrical signal can be applied to more than one location on tissue, e.g., gastrointestinal tissue, of the patient. For non-limiting example, the electrical signal can be applied to two, three, four, or more locations in a distal ileum of the patient. A "location" can be defined by the area of physical contact between the tissue and a means for delivery of the electrical stimulus, e.g., a first electrode of the delivery device 14. Accordingly, the application of the electrical signal to a second location on the tissue of the patient can include contacting a second electrode of the delivery device 14 with a portion of the tissue that is not in physical contact with the first electrode also electrically stimulating the patient.

The electrical signal can have a variety of configurations. Exemplary electrical parameters of the electrical signal that can be varied include frequency, voltage, and pulse duration. The electrical signal can have a frequency of about 0.1 Hz to about 90 Hz; for non-limiting example, the electrical signal can have a frequency of about 0.1 Hz, about 0.15 Hz, about 0.2 Hz, about 0.4 Hz, about 1 Hz, about 4 Hz, about 10 Hz, about 20 Hz, about 25 Hz, about 30 Hz, about 35 Hz, about 40 Hz, about 50 Hz, about 70 Hz, or about 90 Hz. The electrical signal can have a voltage of about 0.5 V to about 25 V; for non-limiting example, the voltage can be about 1 V, about 2 V, about 5 V, about 10 V, about 14V, about 15 V, about 20 V, or about 25 V. The electrical signal can have a pulse duration of about 3 ms to about 500 ms; for non-limiting example, the pulse duration may be about 5 ms, about 50 ms, about 100 ms, about 150 ms, about 200 ms, about 250 ms, about 300 ms, about 350 ms, about 400 ms, about 450 ms, or about 500 ms. In an exemplary embodiment, the electrical signal can be applied at a voltage of about 14V, with a pulse duration of about 5 ms, and at a stimulus frequency of about 20 to about 80 Hz; with respect to such an embodiment, the stimulus frequency can be, for non-limiting example, about 20 Hz, about 40 Hz, or about 80 Hz. In another exemplary embodiment, the electrical signal can be applied at a voltage of about 14 V, with a pulse duration of about 300 ms, and at a frequency of about 0.4 Hz. Various exemplary embodiments of an electrical signal that can be delivered to a patient are described in more detail in U.S. Pat. Pub. No. 2010/0056948 filed Aug. 25, 2009 entitled "Stimulation Of Satiety Hormone Release."

Figure 2:
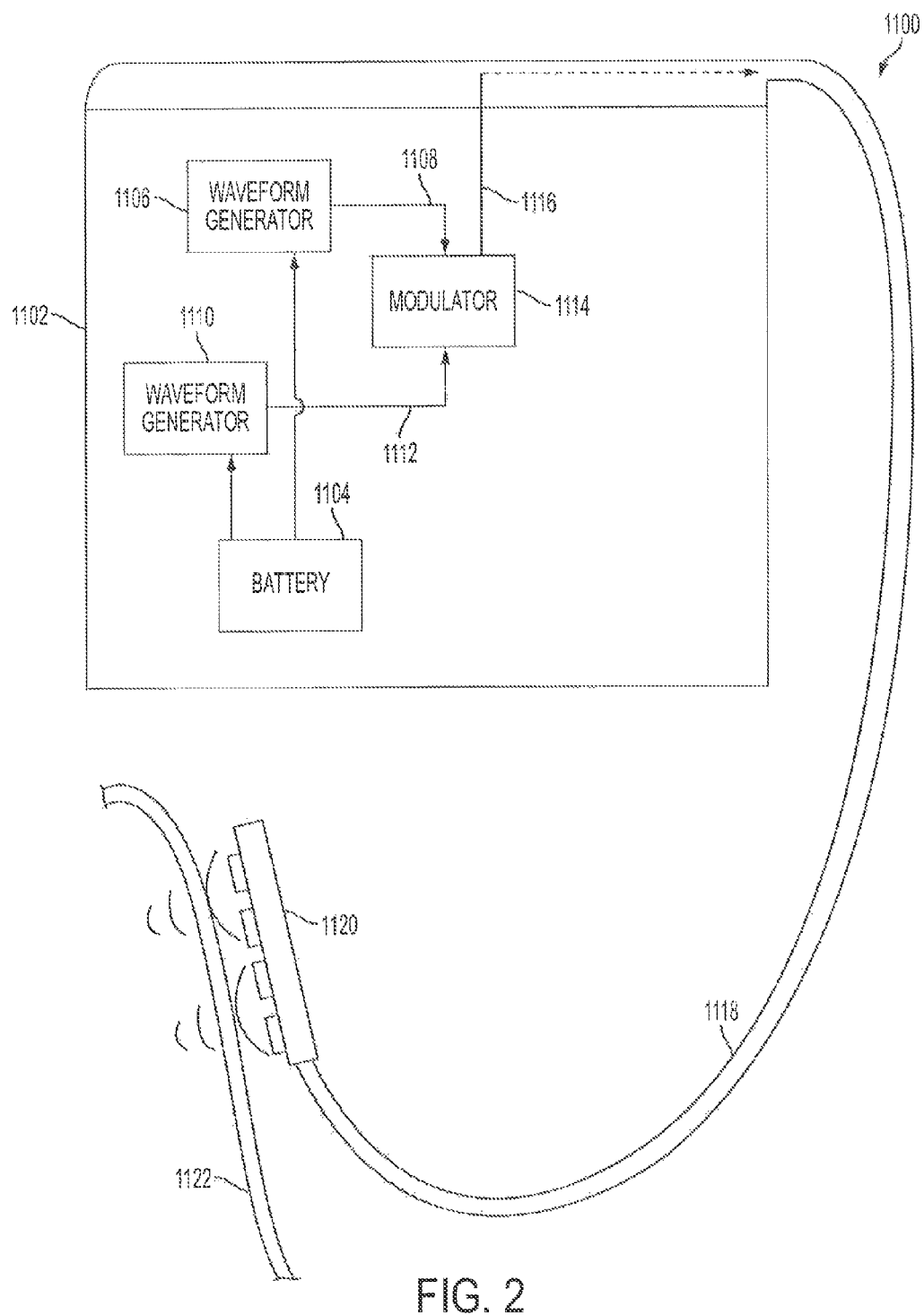
FIG. 2 is a schematic view of one embodiment of an implantable device for electrically stimulating a patient.

An electrical signal can be delivered to the patient in any number of ways to electrically stimulate the patient. FIG. 2 illustrates an exemplary embodiment of a delivery device 1100 configured to generate and deliver an electrical signal to a patient. Although the illustrated delivery device 1100 is implantable, a delivery device configured to deliver electrical stimulation to a patient can be subcutaneously or transcutaneously positioned, as mentioned above. The delivery device 1100 can include a housing 1102 coupled to a suitable power source or battery 1104, such as a lithium battery, a first waveform generator 1106, and a second waveform generator 1108. As in the illustrated embodiment, the battery 1104 and first and second waveform generators can be located within the housing 1102. In another embodiment, a battery can be external to a housing and be wired or wirelessly coupled thereto. The housing 1102 is preferably made of a biocompatible material. The first and second waveform generators 1106, 1108 can be electrically coupled to and powered by the battery 1104. The waveform generators 1106, 1108 can be of any suitable type, such as those sold by Texas Instruments of Dallas, Tex. under model number NE555. The first waveform generator 1106 can be configured to generate a first waveform or low frequency modulating signal 1108, and the second waveform generator 1110 can be configured to generate a second waveform or carrier signal 1112 having a higher frequency than the first waveform 1108. Low frequency modulating signals cannot, in and of themselves, pass through body tissue to effectively stimulate target nerves. The second waveform 1108 can, however, to overcome this problem and penetrate through body tissue. The second waveform 1112 can be applied along with the first waveform 1108 to an amplitude modulator 1114, such as the modulator having the designation On-Semi MC1496, which is sold by Texas Instruments.

Figure 3:
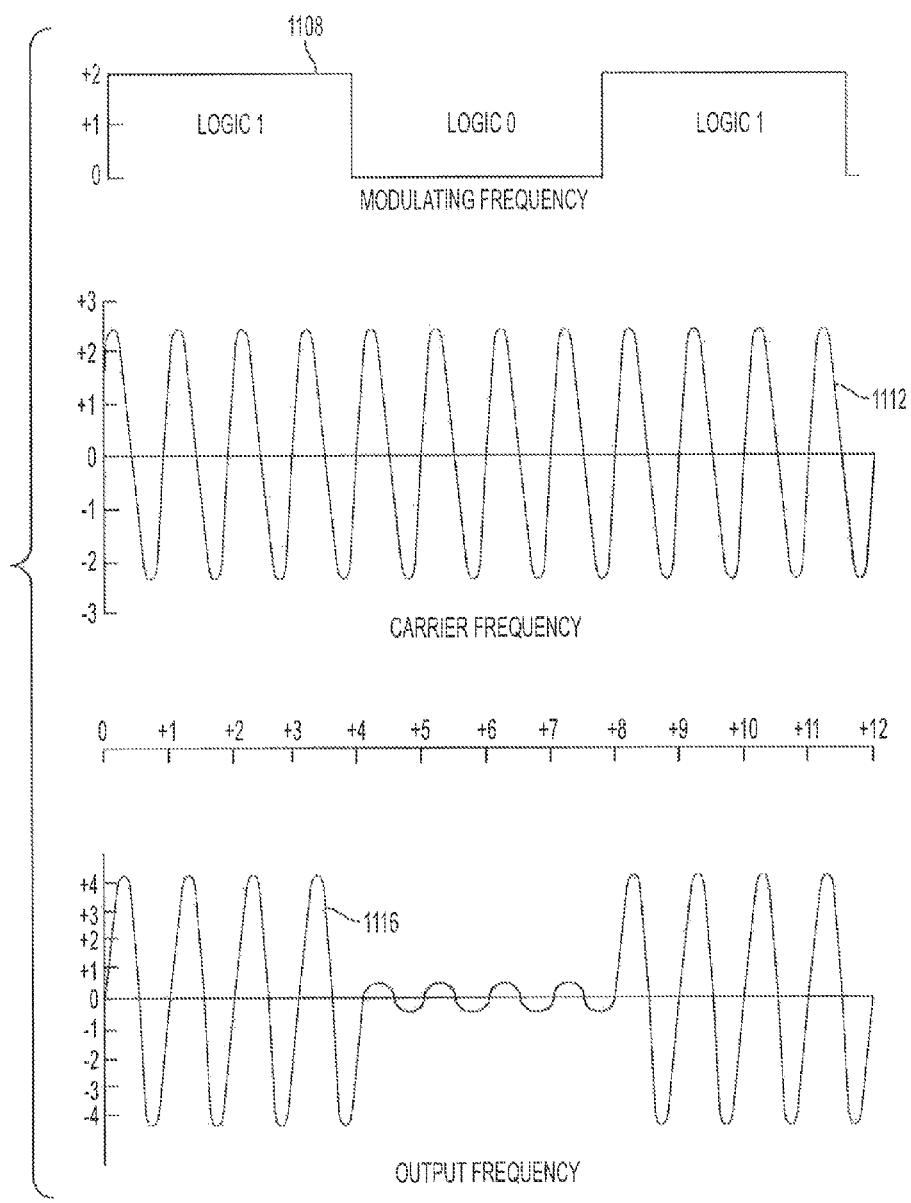
FIG. 3 is a plurality of graphs showing exemplary waveforms generated by the implantable device of FIG. 2.

The modulator 1114 can be configured to generate a modulated waveform 1116 that is transmitted through a lead 1118 to one or more electrodes 1120. Four electrodes are illustrated, but the device 1100 can include any number of electrodes having any size and shape. The lead 1118 can be flexible, as in the illustrated embodiment. The electrodes 1120 can be configured to, in turn, apply the modulated waveform 1116 to a target tissue or nerve 1122 to stimulate the target 1122. The first and second waveforms 1108, 1112 can have any shape, e.g., the first waveform 1108 can be a square wave, and the second waveform 1112 can be a sinusoidal signal. As will be appreciated by a person skilled in the art, modulation of the first waveform 1108 with the second waveform 1112 can result in a modulated waveform or signal 1116 having the configuration shown in FIG. 3. Although the electrical signal in the embodiment illustrated in FIGS. 2 and 3 includes carrier and modulating signals, an electrical signal delivered to a patient can include only one of a carrier and modulating signal.

Various exemplary embodiments of methods and devices for delivering an electrical signal to a patient are described in more detail in U.S. App. Ser. No. 12/980,699 entitled "Methods And Devices For Activating Brown Adipose Tissue," U.S. Pat. Pub. No. 2009/0132018 filed Nov. 16, 2007 and entitled "Nerve Stimulation Patches And Methods For Stimulating Selected Nerves," U.S. Pat. Pub. No. 2010/0056948 filed Aug. 25, 2009 entitled "Stimulation Of Satiety Hormone Release," U.S. Pat. Pub. No. 2008/0147146 filed Dec. 19, 2006 and entitled "Electrode Patch And Method For Neurostimulation," U.S. Pat. Pub. No. 2005/0277998 filed Jun. 7, 2005 and entitled "System And Method For Nerve Stimulation," U.S. Pat. Pub. No. 2006/0195153 filed Jan. 31, 2006 and entitled "System And Method For Selectively Stimulating Different Body Parts," U.S. Pat. Pub. No. 2007/0185541 filed Aug. 2, 2006 and entitled "Conductive Mesh For Neurostimulation," U.S. Pat. Pub. No. 2006/0195146 filed Jan. 31, 2006 and entitled "System And Method For Selectively Stimulating Different Body Parts," U.S. Pat. Pub. No. 2008/0132962 filed Dec. 1, 2006 and entitled "System And Method For Affecting Gastric Functions," U.S. Pat. Pub. No. 2008/0147146 filed Dec. 19, 2006 and entitled "Electrode Patch And Method For Neurostimulation," U.S. Pat. Pub. No. 2009/0157149 filed Dec. 14, 2007 and entitled "Dermatome Stimulation Devices And Methods," U.S. Pat. Pub. No. 2009/0149918 filed Dec. 6, 2007 and entitled "Implantable Antenna," U.S. Pat. Pub. No. 2009/0132018 filed Nov. 16, 2007 and entitled "Nerve Stimulation Patches And Methods For Stimulating Selected Nerves," U.S. patent application Ser. No. 12/317,193 filed Dec. 19, 2008 and entitled "Optimizing The Stimulus Current In A Surface Based Stimulation Device," U.S. patent application Ser. No. 12/317,194 filed Dec. 19, 2008 and entitled "Optimizing Stimulation Therapy Of An External Stimulating Device Based On Firing Of Action Potential In Target Nerve," U.S. patent application Ser. No. 12/407,840 filed Mar. 20, 2009 and entitled "Self-Locating, Multiple Application, And Multiple Location Medical Patch Systems And Methods Therefor," and U.S. patent application Ser. No. 12/605,409 filed Oct. 26, 2009 and entitled "Offset Electrodes."

Various exemplary embodiments of devices configured to directly apply an electrical signal to stimulate nerves are described in more detail in U.S. Pat. Pub. No. 2005/0177067 filed Jan. 26, 2005 and entitled "System And Method For Urodynamic Evaluation Utilizing Micro-Electronic Mechanical System," U.S. Pat. Pub. No. 2008/0139875 filed Dec. 7, 2006 and entitled "System And Method For Urodynamic Evaluation Utilizing Micro Electro-Mechanical System Technology," U.S. Pat. Pub. No. 2009/0093858 filed Oct. 3, 2007 and entitled "Implantable Pulse Generators And Methods For Selective Nerve Stimulation," U.S. Pat. Pub. No. 2010/0249677 filed Mar. 26, 2010 and entitled "Piezoelectric Stimulation Device," U.S. Pat. Pub. No. 2005/0288740 filed Jun. 24, 2004 and entitled, "Low Frequency Transcutaneous Telemetry To Implanted Medical Device," U.S. Pat. No. 7,599,743 filed Jun. 24, 2004 and entitled "Low Frequency Transcutaneous Energy Transfer To Implanted Medical Device," U.S. Pat. No. 7,599,744 filed Jun. 24, 2004 and entitled "Transcutaneous Energy Transfer Primary Coil With A High Aspect Ferrite Core," U.S. Pat. No. 7,191,007 filed Jun. 24, 2004 and entitled "Spatially Decoupled Twin Secondary Coils For Optimizing Transcutaneous Energy Transfer (TET) Power Transfer Characteristics," and European Pat. Pub. No. 377695 published as Int'l. Pat. Pub. No. WO1989011701 published Nov. 30, 2004 and entitled "Interrogation And Remote Control Device."

Another exemplary embodiment of the obesity therapy 18 includes a therapeutic agent, e.g., a natural or an artificial chemical, solution, drug, medicant, neutriceutical, or pharmaceutical administered to patient. In one embodiment, the therapeutic agent can include a nutrient. The nutrient can include any substance configured to provoke a release of one or more hormones from L-cells, such as linoleic acid (LA), a carbohydrate, other sugars, an amino acid, a protein, a fatty acid, a fat, or any combination thereof. The nutrient can take the form of a natural food item; a supplement, e.g., a nutrition drink; or a substance that is made with the express purpose of stimulating L-cells, and therefore need not be a "nutrient" per se in the conventional sense. Generally, delivery of the nutrient to the patient, such as to the patient's intestine, e.g., an ileum of the intestine, can help trigger ileal brake. Normally, the presence of nutrients, which arise from a meal consisting of carbohydrates, fats and proteins, termed "digesta" in the digestive tract, stimulates release of the body's own incretins into the blood stream. Key hormones, released by specialized L-cells located in the mucosa, which is the innermost interior (luminal) wall of the intestines, coordinate the body's response to a meal. The hormones produce this effect by inducing a sense of fullness and cessation of eating (satiety), triggering the release of insulin to maintain proper glucose levels (incretin effect) and slowing the passage of contents through the digestive tract (delaying gastric emptying and slowing small intestinal transit). Collectively, these effects have been termed the ileal brake. By delivering the nutrient, e.g., triggering ileal brake, at the onset of the patient eating solid food, satiation can occur earlier than it would in a normal digestive process without the delivery of the nutrient to the patient. The patient can therefore feel full faster after beginning to eat, thereby encouraging smaller amounts of food intake and, over time, encouraging weight loss. Triggering ileal brake and various exemplary embodiments of nutrients and administration thereof to a patient to help treat obesity are described in more detail in U.S. Pat. Pub. No. 2010/0056948 filed Aug. 25, 2009 entitled "Stimulation Of Satiety Hormone Release."

Figure 4:
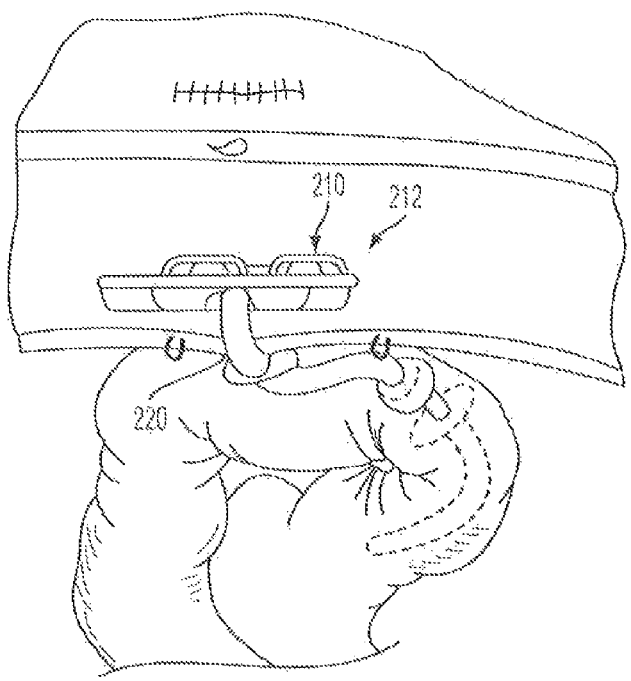
FIG. 4 is a side, partially transparent view of one embodiment of an active agent delivery catheter disposed within an ileum and connected to an active agent reservoir and pump located in subcutaneous fatty tissue.

The nutrient can be delivered to the patient in any number of ways. FIG. 4 illustrates one exemplary embodiment of a delivery device 212, e.g., an active agent catheter delivery system, configured to deliver a nutrient to a patient. The delivery device 212 is shown implanted within an intestine of a patient, but the delivery device 212 can be implanted in a variety of locations and can be implanted in a variety of ways, e.g., implanted laparaoscopically, deployed within the colon through a natural orifice procedure, etc. Various exemplary embodiments, including the delivery device 212, of methods and devices for delivering a nutrient to a patient are described in more detail in U.S. Pat. Pub. No. 2005/0038415 filed Jul. 12, 2004 entitled "Method And Apparatus For Treatment Of Obesity."

Figure 5:
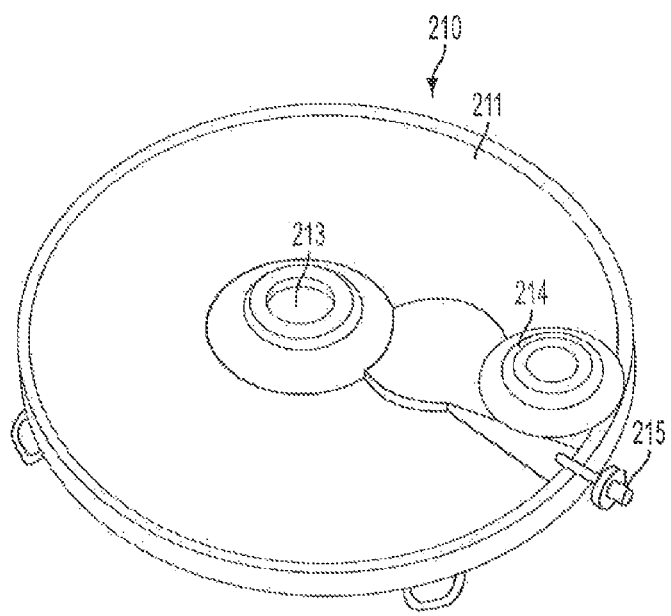
FIG. 5 is a perspective view of the active agent reservoir and pump of FIG. 4.
Figure 6:
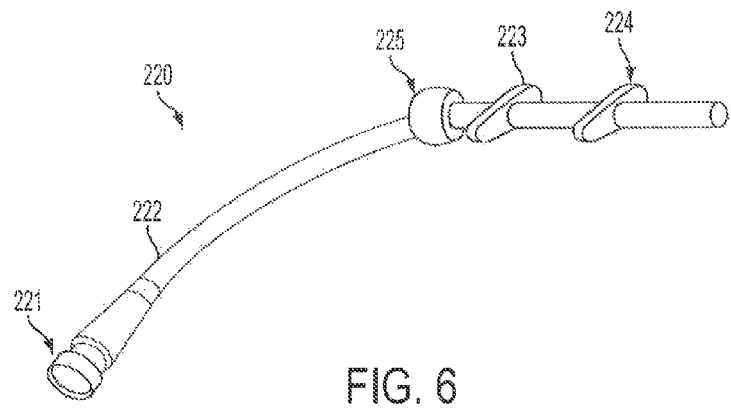
FIG. 6 is a perspective view of the active agent delivery catheter of FIG. 4.

Generally, the delivery device 212 can include an active agent reservoir and pump 210 and an active agent delivery catheter 220. Although any active agent reservoir and pump and active agent delivery catheter can be used, an exemplary embodiment of an active agent reservoir and pump include a Codman® 3000 Infusion Pump, available from Codman & Shurtleff, Inc. of Raynham, Mass., and an exemplary embodiment of an active agent delivery catheter includes a Codman® silicone tapered arterial catheter, available from Codman & Shurtleff, Inc. The reservoir and pump 210 can include any suitable reservoir and/or fluid delivery pump having, as shown in FIG. 5, a resealable fluid insertion boss 213, a fluid reservoir 211, a fluid pump 214, and a radially extended male fluid delivery port 215. In use, a nutrient contained in the reservoir 211 can be dispensed therefrom, through the catheter 220, into the ileum of the patient in order to decrease intestinal motility and increase feelings of satiety experienced by the patient. Optionally, the reservoir 211 can be recharged at any time necessary. Preferably, recharging of the reservoir 211 is performed without removal from the implantation site but is performed remotely such as, for example, by injection with a syringe. The active agent delivery catheter 220, as shown in FIG. 6, can include a female port 221 positioned at a first terminal end of catheter 220 and configured to mate with the male fluid delivery port 215 of the reservoir and pump 210. The catheter 220 can include an elongate fluid transmission lumen 222 extending from the female port 221 to a second terminal end of the catheter 220. Positioned near the second terminal end of the catheter 220 and around a circumference of the lumen 222 can be a first laterally extending brace 223. A second laterally extending brace 224 can positioned distally to the first laterally extending brace 223 in close proximity to the second terminal end of the catheter 220. The catheter 220 can also include a balloon 225 configured to secure the catheter 220 within, e.g., the patient's abdominal cavity, wherein a securing means, such as a row of purse-string sutures, can be placed and tightened around an opening in the intestine to secure the intestine to the catheter 220. The balloon 225 can then be pulled taut against the sealing means to prevent leakage of intestinal contents.

In another exemplary embodiment, the obesity therapy 18 can include delivering both a nutrient and electrical stimulation to the patient. As described in further detail in U.S. Pat. Pub. No. 2010/0056948 filed Aug. 25, 2009 entitled "Stimulation Of Satiety Hormone Release," delivering a nutrient to a patient and electrical stimulating the patient can cause a higher expression of Glucagon-Like Peptide (GLP-1), and hence enhance triggering of ileal brake, than delivery of the nutrient to the patient without electrical stimulation. By triggering delivery of the nutrient and the electrical stimulation relatively quickly after the patient begins eating solid food through the triggering of the delivery device 14 by the processor 16, ileal brake can be further encouraged in a faster fashion than would naturally occur or that would occur if the nutrient was delivered without electrical stimulation. In an exemplary embodiment, and as further discussed in U.S. Pat. Pub. No. 2010/0056948, the electrical signal can be delivered to a tissue of the patient contemporaneously with the contacting of L-cells of the tissue with the nutrient delivered to the patient. "Contemporaneously" generally means that during at least part of the time that the electrical signal is being delivered to the tissue, the L-cells are in direct contact with the nutrient. Thus, if the electrical signal is delivered for a total duration of one second, contacting the L-cells with the nutrient stimulus for 5 seconds after the application of the electrical signal and for 0.1 seconds during the application of the electrical signal will be considered to have been contemporaneous with the application of the electrical signal.

In one exemplary embodiment, a nutrient can be orally administered to a patient, e.g., the patient can swallow a nutrient, e.g., as a pill, a fluid, etc., in conjunction with eating solid food, e.g., at a start of a meal. Stimulation of the patient's L-Cells can be enhanced by electrical stimulation of the patient in the presence of the nutrient, e.g., by a delivery device delivering an electrical signal to the patient. In another exemplary embodiment, a meal that a patient ingests can serve as a stimulus for the patient's L-Cells, which can be amplified by triggered delivery of electrical stimulation to the patient. The meal can be detected in any way, such as heart rate variability, as discussed further below. Since meals can serve to stimulate L-cell production of GLP-1, when properly timed, the electrical stimulation can begin as the meal transits into the patient's duodenum. There is a feed forward signal to the ileum which is responsible for increase in GLP-1 production. This can be enhanced by the presence of electrical stimulation in the intestine.

Figure 7:
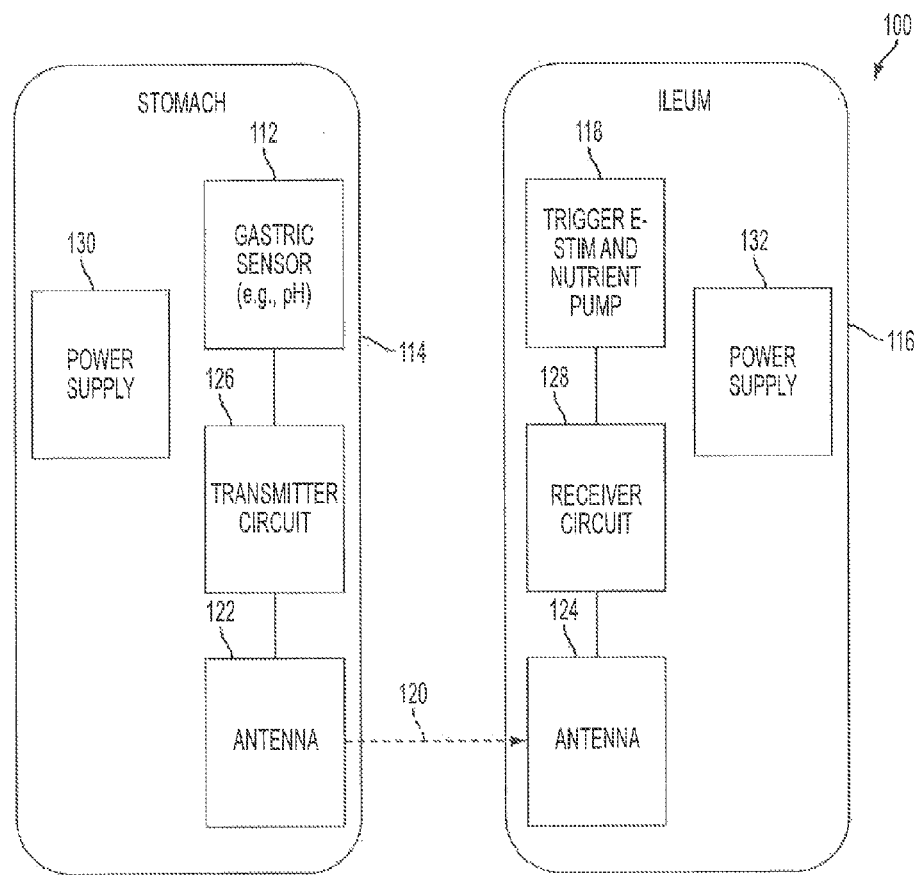
FIG. 7 is a schematic view of one embodiment of an obesity therapy system including a gastric pH sensor, a processor, and a delivery device for delivering an obesity therapy to a patient.

FIG. 7 illustrates one exemplary embodiment of an obesity therapy system 100 including a gastric pH sensor 112 configured to sense gastric pH levels of a patient, a processor 114 having the pH sensor 112 located in a housing thereof, and a delivery device 116 configured to be in communication with the processor 114 and configured to deliver an obesity therapy 118 to the patient. In the illustrated embodiment, the processor 114 and the pH sensor 112 are implanted in a stomach of the patient, and the delivery device 116 is implanted in an ileum of the patient. However, as discussed herein, a sensor and a delivery device can be positioned at the same internal or external anatomical location in a patient's body or at any number of different internal and external anatomical locations. In one embodiment, a pH sensor can be implanted in a patient's stomach, and a housing containing a processor and a delivery device can be implanted within an intestine of the patient, with the processor and the sensor being configured to be in wireless electronic communication with one another such that the sensor can wirelessly transmit the sensed heart rate data to the processor. A person skilled in the art will appreciate that one or more gastric pH sensors can be disposed at a variety of locations within the patient, e.g., the esophagus and the stomach, and each of the pH sensors can be configured to communicate sensed data to the processor 114. The obesity therapy 118 in the illustrated embodiment includes delivery of electrical stimulation and a nutrient, but any one or more obesity therapies can be delivered to the patient in response to a trigger signal 120 from the processor 114.

As in the illustrated embodiment, the pH sensor 112 can be configured to sense gastric pH levels in the stomach. Variations in gastric pH can indicate whether or not there is solid food present in the stomach. The relationship between gastric pH levels and food consumption is described in further detail in "Regional Postprandial Differences in pH Within the Stomach and Gastroesophageal Junction," Digestive Diseases and Sciences, Vol. 50, No. 12 (December 2005), pgs. 2276-2285. Using intraluminal pH sensors to detect eating is described in more detail in "Effects of Thickened Feeding on Gastroesophageal Reflux in Infants: A Placebo-Controlled Crossover Study Using Intraluminal Impedance," Pediatrics 111(4), e355-e359 (April 2003). In general, gastric pH is low in an empty stomach. Upon eating, especially foods that contain protein, gastric pH becomes more basic (i.e., the pH value increases) due to buffering by the food. The increase in pH occurs even though the stomach is actively secreting acid. Once the buffering capacity of the food is exceeded, the gastric pH returns to a low value. Thus, as described in further detail in U.S. Pat. Pub. No. 2009/0192534 filed Jan. 29, 2008 entitled "Sensor Trigger" and in "Regional Postprandial Differences in pH Within the Stomach and Gastroesophageal Junction," Diseases and Sciences, Vol. 50, No. 12 (December 2005), the gastric pH level increases after each meal and returns to the baseline pH sometime thereafter.

The pH sensor 112 can also be configured to communicate the sensed data to a transmitter circuit 126 configured to analyze the sensed data. Based on the analysis, the transmitter circuit 126 can determine whether to transmit the trigger signal 120 to the delivery device 116. In an exemplary embodiment, the processor 114 can be configured to transmit the trigger signal 120 to the delivery device 116 if, based on the sensed data, a change in gastric pH of a selected magnitude occurred, e.g., $|X-Y|$ pH. Alternatively, the processor 114 can be configured to transmit the trigger signal 120 to the delivery device 116 if a change in gastric pH results in a pH range that is less than 7 pH.

As mentioned above, the delivery device 116 can be defaulted to a dormant, sleep, or off mode in which it is not delivering the obesity therapy 118 to the patient. The dormant or off mode can conserve a supply of the obesity therapy 118, e.g., a finite chemical supply stored in a reservoir (not shown) contained within or otherwise coupled to the delivery device 116. The dormant or off mode can also conserve usable power from the device's power supply 132, e.g., an internal battery, capacitor, etc. For non-limiting example, in one exemplary embodiment, the delivery device 116 can be partially dormant such that only the antenna 124 and/or the receiver circuit 128 are powered continuously and another portion of the device 116, such as the obesity therapy 118, is in a dormant, sleep, or off mode. Such a configuration can reduce the power usage of the delivery device 116, thereby reducing the required power capacity of the power supply 132. In one exemplary embodiment, the implantable sensor can be completely shut-off in the dormant, sleep, or off power usage mode. In another embodiment, the dormant, sleep, or off power usage mode can correspond to a low operating frequency, such as an operating frequency of less than or equal to about 1 Hz. At the low operating frequency, some very low power functions can remain active such as a timer and some receiver circuit functions. In general, the use configuration can have an operating frequency in the range of about 2 to 20 Hz. It shall be understood that higher or lower sampling frequencies can be used to conserve more or less power depending upon operational need of the system. Nyquist frequency or Nyquist rate principles can be used to determine the cut-off frequency of a given sampling system. Thus, in one exemplary embodiment, a change in gastric pH detected by the pH sensor 112 that is less than 7 pH can be effective to trigger the delivery device 116, thereby energizing the delivery device 116 from the dormant, sleep, or off mode to a delivery or on mode in which the delivery device 116 can deliver the obesity therapy 118 to the patient.

Similarly, the gastric pH sensor 112 can be defaulted to a dormant, sleep, or off mode in which it is not sensing data or is gathering a limited amount of data, e.g., gathering data at a low sampling rate. Various exemplary embodiments of a sensor having a dormant mode, as well as various exemplary embodiments of powering a system including a sensor and of transmitting signals, are described in further detail in U.S. Pat. Pub. No. 2010/0056948 filed Aug. 25, 2009 entitled "Stimulation Of Satiety Hormone Release" and U.S. Pat. Pub. No. 2009/0192404 filed Jan. 28, 2008 entitled "Methods And Devices For Measuring Impedance In A Gastric Restriction System."

Although the transmitter circuit 126 in the illustrated embodiment is configured to both analyze the sensed data and to generate and transmit the trigger signal 120, as will be appreciated by a person skilled in the art, any one or more processing elements can be configured to perform these and other related actions. As in the illustrated embodiment, the trigger signal 120 can be transmitted from a first antenna 122, which can be located within the processor's housing and in communication with the transmitter circuit 126, to a second antenna 124 located within the delivery device 116. The antennas 122, 124 are in wireless communication in the illustrated embodiment such that the processor 114 and the delivery device 116 are in wireless communication, but as will be appreciated by a person skilled in the art, the processor 114 and the delivery device 116 can be in wired communication with one another. In another embodiment, a processor can be configured to transmit a trigger signal to an external collection device that communicates trigger signal to a delivery device. Similarly, a pH sensor can be configured to transmit a signal to an external collection device that communicates the sensed pH levels to a processor, which can communicate a trigger signal to a delivery device in any direct or indirect and any wired or wireless way. Referring again to the illustrated embodiment of FIG. 7, in response to receipt of the trigger signal 120, a receiver circuit 128 in communication with the second antenna 124 can cause the obesity therapy 118 to be delivered to the patient from the delivery device 116. Although the processor 114 and/or the delivery device 116 can have off-board power supplies, in the illustrated embodiment, the processor 114 and the delivery device 116 have respective first and second on-board power supplies 130, 132, e.g., rechargeable batteries.

Figure 8:
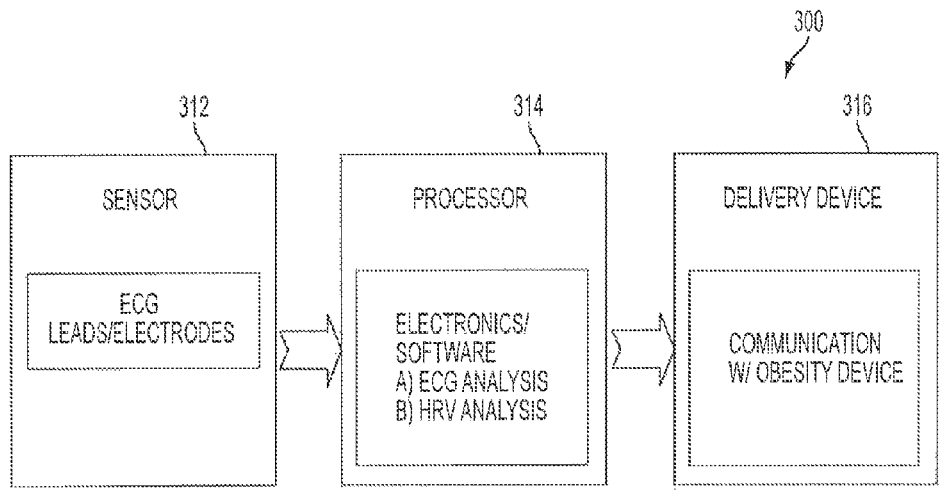
FIG. 8 is a schematic view of one embodiment of an obesity therapy system including a heart rate sensor, a processor, and a delivery device for delivering an obesity therapy to a patient.

FIG. 8 illustrates one exemplary embodiment of an obesity therapy system 300 including a heart rate sensor 312 configured to sense a heart rate of a patient, a processor 314 configured to be in communication with the heart rate sensor 312, and a delivery device 316 configured to be in communication with the processor 314 and configured to deliver an obesity therapy (not shown) to the patient. A person skilled in the art will appreciate that one or more heart rate sensors can be disposed at a variety of locations around the patient, e.g., the wrist and the sternum, and each of the heart rate sensors can be configured to communicate sensed data to the processor 314. As discussed above, all of the heart rate sensor 312, the processor 314, and the delivery device 316 can be implanted within the patient, all can be positioned external to the patient, or a combination thereof with one or more being positioned subcutaneously and one or more being positioned transcutaneously.

Figure 9:
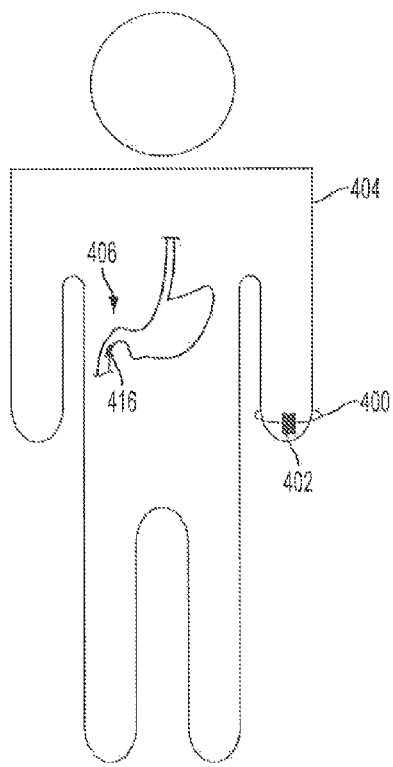
FIG. 9 is a schematic, partially transparent view showing a patient wearing one embodiment of a band having a housing attached thereto and configured to communicate with one embodiment of a delivery device positioned within an intestine of the patient.

For example, as shown in one exemplary embodiment in FIG. 9, a band 400 attached to a housing 402, similar to a watch band and a watch housing, can be configured to be transcutaneously positioned around a wrist of a patient 404. The band 400 and the housing 402 can be configured to be removed from the patient 404 and discarded, repaired such as replacing a low battery, reprogrammed such as to analyze sensed data in a different way or change what data determination triggers transmission of a trigger signal to a delivery device 416, and/or relocated to another position, e.g., relocated from a right wrist to a left wrist. The housing 402 can have contained therein a processor (not shown) configured to be in communication with the a heart rate sensor (not shown) attached to the band 400. The heart rate sensor can be configured to sense a heart rate of the patient 404, e.g., using a heart rate sensing electrode (not shown) contacting an exterior skin surface of the patient 404, as will be appreciated by a person skilled in the art. The processor in the housing 402 can be configured to analyze heart rate data gathered by the sensor and to communicate a trigger signal to the delivery device 416 implanted within an intestine 406 of the patient 404. Although, in other embodiments, the processor can be included in an external device, e.g., a portable computer, a desktop computer, a handheld electronic device such as a mobile phone, etc., as will be appreciated by a person skilled in the art. The external device can be configured to receive sensed data from the sensor, to analyze the sensed data, and to transmit a trigger signal to the deliver device based upon results of the processor's analysis. Referring again to FIG. 9, the delivery device 416 can be configured to deliver an obesity therapy, e.g., electrical stimulus and/or a nutrient, to the patient 404 when triggered to do so by receipt of the trigger signal. Although the delivery device 416 is implanted within the patient 404, as discussed above, the delivery device 416 can be implanted in any other location or can be located external to the patient 404. Further, while only one delivery device 416 is shown in the illustrated embodiment, any number of delivery devices can be implanted within or externally coupled to the patient 404 to deliver one or more obesity therapies thereto. If multiple delivery devices are coupled to the patient 404, the processor can be configured to transmit a trigger signal to each of the delivery devices, e.g., a separate trigger signal transmitted to each of the delivery devices, to cause each of the delivery devices to start delivery of an obesity therapy to the patient 404. In some embodiments, the processor can be configured to trigger a first number of the multiple delivery devices based on a first determination of analyzed sensed data, e.g., a change in heart rate over a first threshold value, and to trigger a second number of the multiple delivery devices, which can include one or more of the same devices in the first number of devices, based on a second determination of analyzed sensed data, e.g., a change in heart rate over a second threshold value.

Other exemplary embodiments of externally located heart rate sensors include a strap configured to be worn by a patient such that a heart rate sensing electrode attached to the strap is positioned on an exterior skin surface of a chest of the patient, a heart rate sensing electrode attached to an article of clothing configured to be worn by a patient such that the electrode contacts an exterior skin surface of the patient, and a pulse oximeter configured to be positioned on an external skin surface of a finger of a patient. An externally located heart rate sensor can allow an obesity therapy to be delivered to a patient without requiring surgery to implant the sensor, thereby reducing, if not eliminating, adverse side effects and potential complications from surgery. If a delivery device configured to be triggered based on data gathered by the externally located heart rate sensor is also transcutaneously positioned, e.g., in the form of a transdermal patch configured to electrically stimulate the patient, then the patient can be effectively treated without requiring any surgery, thereby eliminating adverse side effects and potential complications from surgery. However, as will be appreciated by a person skilled in the art, the patient can also undergo a surgical procedure to treat severe obesity either before or after treatment using an obesity therapy delivered as described herein. Exemplary embodiments of a heart rate sensor configured to be positioned within a patient include a lead configured to be implanted within a heart of the patient, and an electrode configured to be implanted on a thorax of the patient.

Referring again to FIG. 8, the heart rate sensor 312 can be configured to gather heart rate data, e.g., electrocardiogram (ECG) signals and/or electrogastrography (EGG) signals, using at least one lead and/or at least one electrode (not shown) and to communicate the sensed data to the processor 314. The processor 314 can be configured to detect a change in heart rate, e.g., heart rate variability (HRV), of the patient 404 by analyzing the ECG signals sensed by the sensor 312 and determine if the HRV indicates an onset of the patient eating a solid food. Changes in heart rate can occur after ingestion of solid food, as discussed for example in Friesen et al., "Autonomic Nervous System Response To A Solid Meal And Water Loading In Healthy Children: Its Relation To Gastric Myoelectrical Activity," Neurogastroenterol Motil. 19(5): 376-382 (2007); Friesen et al., "The Effect Of A Meal And Water Loading On Heart Rate Variability In Children With Functional Dyspepia," Dig Dis Sci 55: 2283-2387 (2010); Yin et al., "Inhibitory Effects Of Stress On Postprandial Gastric Myoelectrical Activity And Vagal Tone In Healthy Subjects," Neurogastroenterol Motil 16(6): 737-744 (December 2004); Watanabe et al., "Effects of water ingestion on gastric electrical activity and heart rate variability in healthy subjects," J Auton Neuro Syst 58(1-2): 44-50 (1996); and Lipsitz et al., "Hemodynamic And Autonomic Nervous System Responses To Mixed Meal Ingestion In Healthy Young And Old Subjects And Dysautonomic Patients With Postprandial Hypotension," Circulation, 87: 391-400 (1993).

HRV analysis can be performed in a variety of ways, such as using time-domain and/or frequency-domain methods, as will be appreciated by a person skilled in the art. Generally, the time-domain methods can include calculations directly from raw R-R interval time series data, e.g., raw data of times from the peak of one R to the next R peak in a QRS complex of an echocardiogram, such as by using the standard deviation of all normal R-R intervals (SDNN), the standard deviation of the successive differences (SDSD) between R-R intervals, etc. Generally, the frequency-domain methods can include calculating a power spectral density (PSD) of R-R interval time series data. Calculating the PSD can be divided into nonparametric, e.g., fast Fourier transform (FFT) based calculations and parametric, e.g., autoregressive model, calculations. The PSD can be analyzed by calculating power and peak frequencies for different frequency bands, such as a very low frequency (VLF) band, e.g., in a range of about 0 to 0.04 Hz), a low frequency (LF) band, e.g., in a range of about 0.04 to 0.15 Hz), and a high frequency (HF) band, e.g., in a range of about 0.15 to 0.4 Hz). The LF band can represent sympathetic activity, and the HF band can represent parasympathetic activity. In healthy, normal patients after ingesting a solid meal, power in the LF band increases, while power in the HF band decreases. Analysis of LF and HF bands can therefore result in a determination that a patient is eating when power in the LF band increases a certain threshold amount while power in the HF band decreases a threshold amount. Accordingly, in an exemplary embodiment, the processor 314 can analyze a power spectral density in LF and HF bands to determine onset of the patient eating a solid food, and send the trigger signal to the delivery device 316 accordingly. In one embodiment, the processor 314 can determine a total power increase from 30.4+/−25.5 units to 63.0+/−48.5 units 80 minutes after ingestion of solid food, and an LF increase of 24.7+/−19.7 units to 55.8+/−44 after 80 min. The units are arbitrary due to normalization. Such parameters are described in further detail in Lipsitz et al., "Hemodynamic And Autonomic Nervous System Responses To Mixed Meal Ingestion In Healthy Young And Old Subjects And Dysautonomic Patients With Postprandial Hypotension," Circulation, 87: 391-400 (1993). In another embodiment, the processor 314 can determine an LF to HF ratio increase of 1.78+/−0.33 to 2.5+/−0.49 units 30 minutes after ingestion of solid food, and an HF decrease of 21.8+/−4.2 to 16+/−0.5 after 30 min. The units are arbitrary due to normalization. Such parameters are described in further detail in Lu et al, Digestive Diseases and Sciences, Vol 44 (4) 857-861.

Assessments of heart rate variability can be used to detect a wide range of physiologic functions in addition to eating. Non-limiting example of such physiologic functions include bladder control (such as bladder and urge incontinence), sexual dysfunction (such as erectile dysfunction), chronic constipation, fecal incontinence, obstructive sleep apnea, pain management (such as post-operative pain, chronic low back pain, lower urinary tract pain, and other chronic pain syndromes), blood pressure control, cardiac ischemia detection, heart failure therapy, GERD, and gastroparesis.

In another exemplary embodiment of an obesity therapy system, the system can include a gastric pH sensor configured to sense gastric pH levels of a patient similar to that discussed above regarding the sensor 112 of FIG. 7, a heart rate sensor configured to sense a heart rate of the patient similar to that discussed above regarding the sensor 312 of FIG. 8, a processor configured to receive gathered pH data from the gastric pH sensor and gathered heart rate data from the heart rate sensor, and a delivery device configured to deliver an obesity therapy to the patient upon receipt of a trigger signal from the processor. By providing the processor with gastric pH data and heart rate data, the processor can analyze both sets of data, separately or together, and more accurately determine onset of the patient eating solid food.

In some embodiments of an obesity therapy system, heart rate data and/or gastric pH data can be gathered for a patient and analyzed by a processor in addition to one or more additional sets of sensed data that can indicate whether the patient is eating. The additional set(s) of data can generally include data that can indicate whether a patient has begun eating solid food. The processor considering data related to a plurality of different factors, e.g., heart rate, gastric pH, impedance, gastric stretch, etc., can help provide redundancy in case of sensor and/or communication failure, and can help increase accuracy in determining that an onset of solid food has begun. One embodiment of such eating indicator data includes data of impedance across a stomach wall of the patient. Collecting gastric impedance data and/or using changes in gastric impedance to detect eating is described in more detail in U.S. Pat. Pub. No. 2009/0192404 filed Jan. 28, 2008 entitled "Methods And Devices For Measuring Impedance In A Gastric Restriction System," Silny et al, "Verification of the intraluminal multiple electrical impedance measurement for the recording of gastrointestinal motility," Nuerogastroenterology & Motility, Vol 5(2): 107-122 (June 1993); "Effects of Thickened Feeding on Gastroesophageal Reflux in Infants: A Placebo-Controlled Crossover Study Using Intraluminal Impedance," Pediatrics 111(4), e355-e359 (April 2003). Another embodiment of such eating indicator data includes data related to gastric stretch. Various embodiments of collecting and/or analyzing gastric stretch data to determine eating are described in more detail in Paintal, et al., "A Study Of Gastric Stretch Receptors: Their Role In The Peripheral Mechanisms Of Satiation Of Hunger And Thirst," Journal of Physiology, Vol. 126, 255-270 (1954), and Geliebter et al., "Gastric Distension By Balloon And Test-Meal Intake In Obese And Lean Subjects," Am J Clin Nutr, Vol 48, 592-594 (1988).

The devices disclosed herein can be designed to be disposed of after a single use, or they can be designed to be used multiple times. In either case, however, the device can be reconditioned for reuse after at least one use. Reconditioning can include any combination of the steps of disassembly of the device, followed by cleaning or replacement of particular pieces, and subsequent reassembly. In particular, the device can be disassembled, and any number of the particular pieces or parts of the device can be selectively replaced or removed in any combination, e.g., electrodes, a battery or other power source, an externally wearable sensor and/or housing therefor, etc. Upon cleaning and/or replacement of particular parts, the device can be reassembled for subsequent use either at a reconditioning facility, or by a surgical team immediately prior to a surgical procedure. Those skilled in the art will appreciate that reconditioning of a device can utilize a variety of techniques for disassembly, cleaning/replacement, and reassembly. Use of such techniques, and the resulting reconditioned device, are all within the scope of the present application.

Preferably, the invention described herein will be processed before surgery. First, a new or used instrument is obtained and if necessary cleaned. The instrument can then be sterilized. In one sterilization technique, the instrument is placed in a closed and sealed container, such as a plastic or TYVEK bag. The container and instrument are then placed in a field of radiation that can penetrate the container, such as gamma radiation, x-rays, or high-energy electrons. The radiation kills bacteria on the instrument and in the container. The sterilized instrument can then be stored in the sterile container. The sealed container keeps the instrument sterile until it is opened in the medical facility.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. A medical system, comprising:
   a sensor configured to be positioned in contact with a tissue of a patient, the sensor being configured to sense a heart rate of the patient;
   a processor configured to be in communication with the sensor and to analyze the sensed heart rate to detect a change in heart rate of the patient by analyzing electrocardiogram (ECG) signals sensed by the sensor, the analyzing comprising analyzing a power spectral density in low frequency and high frequency bands such that the processor determines onset of the patient eating a solid food; and
   a delivery device configured to be implanted within the patient and to be in communication with the processor, the delivery device being defaulted to a dormant mode in which the delivery device does not deliver an obesity therapy to the patient, and the delivery device being configured to change from the dormant mode to a delivery mode, in which the delivery device delivers the obesity therapy to the patient, in response to the processor detecting the change in heart rate and determining the onset of the patient eating the solid food.

2. The system of claim 1, wherein the delivery device is configured to change from the delivery mode to the dormant mode upon occurrence of a predetermined trigger event, and is configured to repeatedly change between the delivery and dormant modes based on the processor detecting changes in heart rate of the patient and determining the onset of the patient eating a solid food, and based on occurrences of the predetermined trigger event.

3. The system of claim 2, wherein the predetermined trigger event comprises passage of a predetermined amount of time during which the delivery device is in the delivery mode.

4. The system of claim 1, wherein the processor is configured to be implanted within the patient.

5. The system of claim 1, wherein the processor is configured to be transcutaneously positioned.

6. The system of claim 1, wherein the sensor is configured to be implanted within the patient.

7. The system of claim 6, wherein the sensor comprises at least one of a lead configured to be implanted within a heart of the patient, and an electrode configured to be implanted on a thorax of the patient.

8. The system of claim 1, wherein the sensor is configured to be transcutaneously positioned such that the sensor is in direct contact with an exterior skin surface of the patient.

9. The system of claim 8, wherein the sensor comprises at least one of a first electrode attached to a strap configured to be worn by the patient such that the first electrode is positioned on an exterior skin surface of a chest of the patient, a second electrode attached to an article of clothing configured to be worn by the patient such that the second electrode contacts an exterior skin surface of the patient, a pulse oximeter configured to be positioned on an external skin surface of a finger of the patient, and a third electrode attached to a band configured to be positioned around a wrist of the patient such that the third electrode contacts an exterior skin surface of a wrist of the patient.

10. The system of claim 1, wherein the obesity therapy comprises at least one of electrical stimulation and administration of a therapeutic agent to the patient.

11. The system of claim 10, wherein the therapeutic agent comprises a nutrient configured to provoke a release of one or more hormones from L-cells of the patient.

12. The system of claim 1, wherein the processor is configured to transmit data indicating an amount of the solid food eaten by the patient to the delivery device, the delivery device being configured to determine an amount of the obesity therapy to deliver to the patient based on the transmitted data.

13. A medical method, comprising:
   positioning a sensing device in contact with tissue of a patient;
   positioning a delivery device in contact with tissue of the patient, the delivery device including an obesity therapy and being in a default off configuration in which the delivery device does not deliver the obesity therapy to the patient;
   detecting a change in heart rate of a patient using heart rate data gathered by the sensing device by analyzing a power spectral density in low frequency and high frequency bands of the heart rate data to determine onset of the patient eating a solid food; and
   in response to the determined onset of the patient eating the solid food and the detected change in heart rate, changing the delivery device from the default off configuration to an on configuration in which the delivery device delivers the obesity therapy to the patient.

14. The method of claim 13, further comprising:
detecting the onset of the patient eating the solid food and the change in heart rate using a processor remotely located from the delivery device; and
transmitting the change in heart rate from the processor to the delivery device to trigger the changing.

15. The method of claim 13, wherein positioning the sensing device comprises transdermally positioning the sensing device such that the sensing device is in direct contact with an exterior skin surface of the patient.

16. The method of claim 13, wherein positioning the sensing device comprises implanting the sensing device within the patient.

17. The method of claim 13, wherein delivering the obesity therapy comprises at least one of electrically stimulating the patient and administering a therapeutic agent to the patient.

18. The method of claim 13, further comprising orally administering a nutrient to the patient in conjunction with the patient eating solid food, and wherein the obesity therapy comprises electrically stimulating the patient.

19. The method of claim 13, further comprising changing the delivery device from the on configuration to the off configuration after a predetermined amount of time has passed after the determined onset of the patient eating the solid food and the detected change in heart rate.

20. The method of claim 13, further comprising determining that the patient has ceased eating the solid food, and changing the delivery device from the on configuration to the off configuration in response to the determination that the patient has ceased eating the solid food.

21. The method of claim 13, further comprising determining subsequent onsets of the patient eating solid food, wherein the delivery device is only changed from the default off configuration to the on configuration in response to the determined onset of the patient eating the solid food and in response to the subsequent determinations of onsets of the patient eating solid food.

\* \* \* \* \*